(12) United States Patent
Holland

(10) Patent No.: US 10,926,037 B2
(45) Date of Patent: Feb. 23, 2021

(54) SYRINGE PLUNGER, BUNG AND SYRINGE

(71) Applicant: OWEN MUMFORD LIMITED, Oxfordshire (GB)

(72) Inventor: Damian Alexander Holland, Oxfordshire (GB)

(73) Assignee: Owen Mumford Limited, Oxford (GB)

( * ) Notice: Subject to any disclaimer, the term of this patent is extended or adjusted under 35 U.S.C. 154(b) by 110 days.

(21) Appl. No.: 15/570,490

(22) PCT Filed: Apr. 4, 2016

(86) PCT No.: PCT/GB2016/050951
§ 371 (c)(1),
(2) Date: Oct. 30, 2017

(87) PCT Pub. No.: WO2016/174389
PCT Pub. Date: Nov. 3, 2016

(65) Prior Publication Data
US 2018/0147361 A1    May 31, 2018

(30) Foreign Application Priority Data
Apr. 29, 2015   (GB) ..................................... 1507297

(51) Int. Cl.
*A61M 5/315*    (2006.01)
*A61M 5/00*     (2006.01)

(52) U.S. Cl.
CPC .......... *A61M 5/31513* (2013.01); *A61M 5/00* (2013.01); *A61M 5/315* (2013.01);
(Continued)

(58) Field of Classification Search
CPC .... A61M 2005/31516; A61M 5/31513; A61M 5/31515; A61M 5/178
(Continued)

(56) References Cited

U.S. PATENT DOCUMENTS 3,045,674 A * 7/1962 Goldberg ........... A61M 5/31511
                                                     604/228
3,834,387 A * 9/1974 Brown .............. A61M 5/31513
                                                     604/125
(Continued)

FOREIGN PATENT DOCUMENTS

DE   10 2005 003516 B3   4/2006
EP      0 575 917 A2    12/1993
(Continued)

OTHER PUBLICATIONS

International Search Report, dated Jul. 12, 2016, from corresponding PCT/GB2016/050951 application.
(Continued)

*Primary Examiner* — Brandy S Lee
*Assistant Examiner* — Nidah M Hussain
(74) *Attorney, Agent, or Firm* — Quarles & Brady LLP

(57) ABSTRACT

A syringe plunger, bung and/or syringe is disclosed. The syringe plunger includes an elongate shaft for insertion into a barrel of a syringe, wherein an end of the shaft is configured for slidable engagement within a recess in a bung of the syringe such that the end of the shaft abuts a surface of the recess, and wherein the end of the shaft is further configured such that, after engagement between the end of the shaft and the recess, a relative force therebetween longitudinally deforms the bung.

13 Claims, 2 Drawing Sheets

(52) U.S. Cl.
CPC ............... *A61M 5/31515* (2013.01); *A61M 2005/31516* (2013.01); *A61M 2205/0216* (2013.01)

(58) Field of Classification Search
USPC ........................................ 604/222
See application file for complete search history.

(56) References Cited

U.S. PATENT DOCUMENTS

| | | | | |
|---|---|---|---|---|
| 4,391,272 | A | * | 7/1983 | Staempfli ............ A61M 5/508 604/110 |
| 5,411,489 | A | * | 5/1995 | Pagay ............... A61M 5/31513 604/218 |
| 10,030,771 | B2 | * | 7/2018 | Shimizu .................... F16J 9/20 |
| 2003/0187406 | A1 | | 10/2003 | Spofforth |
| 2012/0271245 | A1 | * | 10/2012 | Achan, Jr. .......... A61M 5/31511 604/236 |

FOREIGN PATENT DOCUMENTS

| | | |
|---|---|---|
| EP | 0 758 255 A1 | 2/1997 |
| WO | 2005/070484 A1 | 8/2005 |
| WO | 2005/070485 A1 | 8/2005 |
| WO | 2006/020953 A1 | 2/2006 |

OTHER PUBLICATIONS

GB Search Report, dated Oct. 1, 2015, from corresponding GB1507297.8 application.

\* cited by examiner

SYRINGE PLUNGER, BUNG AND SYRINGE

TECHNICAL FIELD

The invention relates to syringe plungers, bungs and/or syringes. More specifically, the invention relates to, but is not limited to, syringe plungers, bungs and/or syringes configured to longitudinally deform a bung positioned in a barrel of a syringe.

BACKGROUND

Syringes comprise a barrel having an aperture end from which the contents of the barrel may be expelled and an open end into which a bung and syringe plunger may be inserted. The bung is configured to move within a barrel of a syringe in order to expel the contents of the barrel from the aperture end. The syringe plunger comprises an elongate shaft configured to enter the barrel and arranged such that a force applied to the shaft is transferred to the bung, which travels within the barrel towards the aperture end.

Referring to FIG. 1, a needle end of a typical syringe 10 is shown. The aperture end 12 of the barrel comprises an aperture 14 that is narrower than an internal diameter of the barrel 16 and a shoulder 18 extending radially outward from the aperture towards a wall of the barrel 16. The shoulder may be angled or curved such that the aperture end 12 of the barrel 16 defines a hemispherical, conical or frusto-conical shape, or another shape narrowing towards the aperture 14. However, a bung 20 has a substantially flat surface 22 facing the aperture, which results in some of the contents of the barrel 16 remaining in the barrel after completion of an inward stroke of the syringe plunger.

SUMMARY

Exemplary syringe plungers, bungs and/or syringes described herein seek to mitigate or solve at least the abovementioned problem. Generally, exemplary syringe plungers, bungs and/or syringes are configured for slidable engagement between the syringe plunger and the bung, such that when the bung reaches the end of the wall of the barrel, continued force applied to the syringe plunger longitudinally deforms the bung to fill the aperture end of the barrel.

According to the invention in a first aspect, there is provided a syringe plunger, comprising: an elongate shaft for insertion into a barrel of a syringe, wherein an end of the shaft is configured for slidable engagement within a recess in a bung of the syringe such that the end of the shaft abuts a surface of the recess, and wherein the end of the shaft is further configured such that, after engagement between the end of the shaft and the recess, a relative force therebetween longitudinally deforms the bung.

The longitudinal deformation of the bung allows the end surface of the bung that faces the aperture to move into the very end of the barrel after the inward stroke of the bung is complete. The slidable engagement of the syringe plunger with the bung allows further insertion of the syringe plunger into the recess of the bung, thereby causing the deformation.

Optionally, the end of the shaft comprises an engagement pin.

Optionally, the engagement pin comprises a substantially flat pin sidewall wall.

Optionally, the engagement pin comprises a deformation surface configured to abut a base of the recess in the bung.

Optionally, the engagement pin has a conical or frusto-conical shape.

Optionally, the engagement pin has a length greater than a depth of the recess in the bung, such that continued insertion of the engagement pin into the recess after abutment of the deformation surface with the base of the recess deforms the bung.

Optionally, the shaft further comprises a limiting shoulder configured to limit an insertion distance of the shaft within the recess of the bung.

According to the invention in a second aspect, there is provided a bung for use in a barrel of a syringe and comprising a recess configured to slidably engage with an end of a shaft of a syringe plunger, such that the end of the shaft abuts a surface of the recess, and wherein the bung is further configured such that, after engagement between the end of the shaft and the recess, a relative force therebetween longitudinally deforms the bung.

Optionally, the recess comprises substantially flat sidewalls.

Optionally, the surface of the recess comprises a base of the recess.

Optionally, the recess has a conical or frusto-conical shape.

Optionally, the recess has a depth less than a length of the end of the shaft, such that continued insertion of the end of the shaft into the recess after abutment of the end of the shaft with the surface of the recess deforms the bung.

Optionally, the bung comprises a resiliently deformable material.

According to the invention in a third aspect, there is provided a syringe comprising: an elongate shaft for insertion into a barrel of the syringe; and a bung comprising a recess, wherein an end of the shaft is configured for slidable engagement within the recess in the bung such that the end of the shaft abuts a surface of the recess, and wherein the end of the shaft and the recess in the bung are further configured such that, after engagement between the end of the shaft and the recess, a relative force therebetween longitudinally deforms the bung.

DETAILED DESCRIPTION

Figure 1:
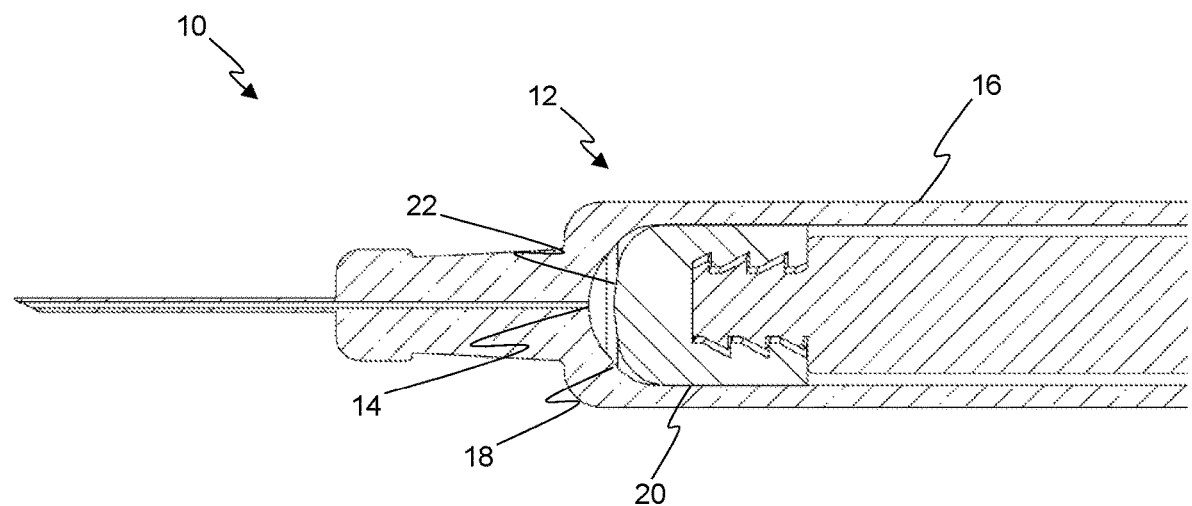
FIG. 1 shows a section through an aperture end of a syringe.
Figure 2:
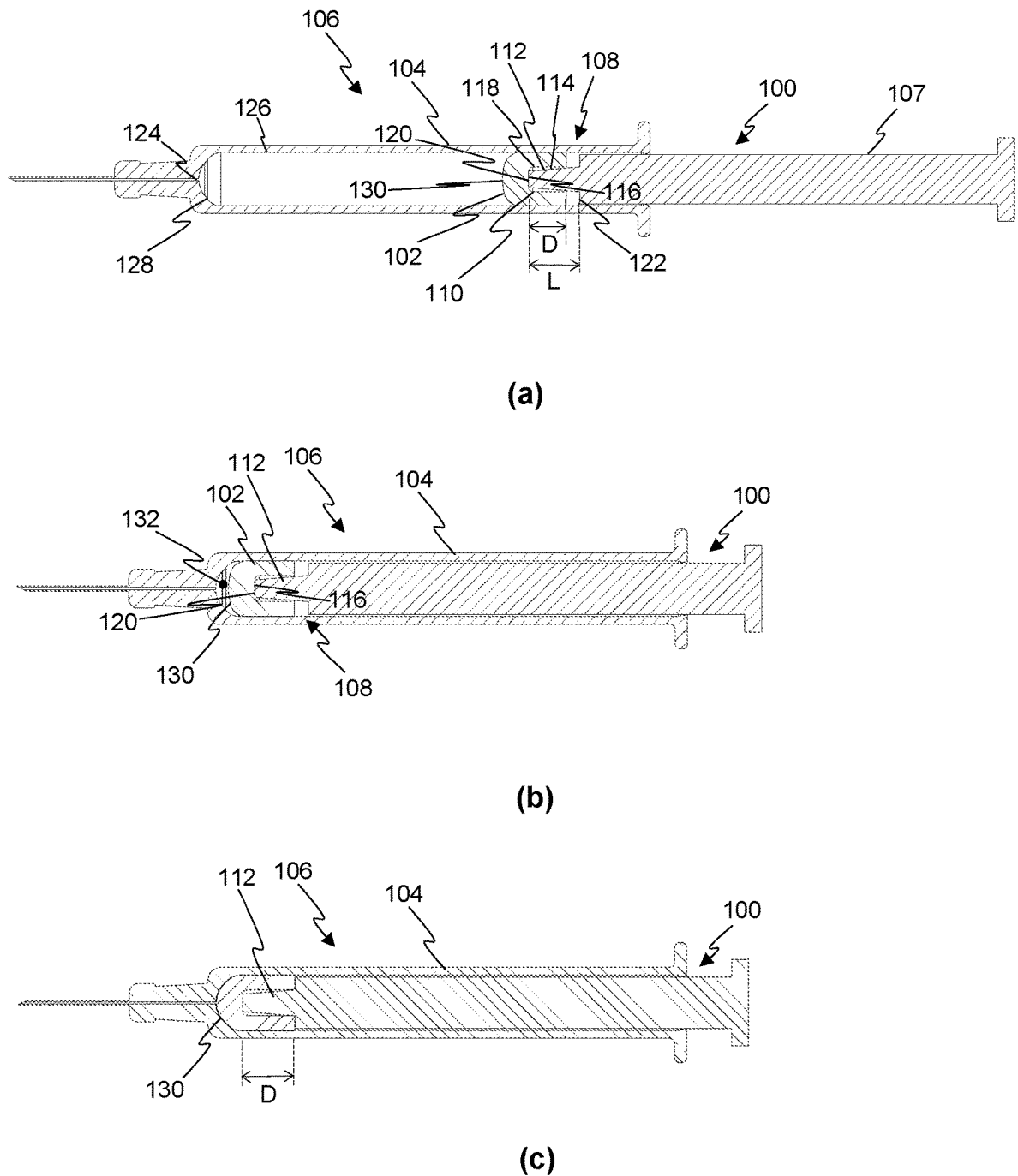
FIGS. 2a-2c show sections through a syringe at different points along an inward stroke of a syringe plunger.

FIG. 2a shows an exemplary syringe plunger 100 that is engaged with a bung 102 positioned within a barrel 104 of a syringe 106. The syringe plunger 100 is extended.

The syringe plunger 100 comprises an end 108 that is configured for slidable engagement with a recess 110 of the bung 102. The syringe plunger 100 comprises an elongate shaft 107 and an end 108.

In an exemplary apparatus, the end 108 of the syringe plunger 100 is configured to enter the recess 110 and leave the recess 110 freely. In such apparatus, the end 108 of the syringe plunger 100 is not held within the recess 110. In another exemplary apparatus, the end 108 of the syringe plunger 100 may be held in an engaged position with the bung 102, but the end 108 may be able to slide further in and/or out of the recess 110, for example, by deformation of the bung 102. In such exemplary apparatus, the end 108 of the syringe plunger may be fixed, for example by a glue or resin, to a base of the recess 110 while allowing relative movement of the end 108 and the sidewalls of the recess 110.

It is noted that the term "slidable" should not necessarily be limited to syringe plungers and bungs configured such that the end 108 of the syringe plunger 100 is in contact with a wall of the recess 110 during or after engagement.

In exemplary apparatus, the end 108 of the syringe plunger 100 comprises an engagement pin 112 having pin sidewalls 114 and a deformation surface 116. As used herein, the term "end of the syringe plunger" and "engagement pin" may have the same meaning. The recess 110 comprises recess sidewalls 118 and a base 120. The pin sidewalls 114 are substantially flat such that they may move with respect to the recess sidewalls 118. The recess sidewalls 118 are substantially flat. In the exemplary apparatus of FIG. 2, the engagement pin 112 forms a substantially frusto-conical shape. The deformation surface 116 of the engagement pin 112 is configured to abut the base 120 of the recess 110 when the engagement pin 112 is engaged with the recess 110.

The length L of the engagement pin 112 is greater than the depth D of the recess 110. This allows the engagement pin 112 to enter the recess 110 further during longitudinal deformation of the bung 102.

The end 108 of exemplary syringe plungers 100 comprise a limiting shoulder 122. The limiting shoulder may be configured to limit the insertion of the engagement pin 112 into the recess 110.

The bung 102 is longitudinally deformable. That is, the bung may be deformed along a longitudinal axis of the syringe 106 in which it is fitted. In exemplary apparatus, the bung 102 may be longitudinally elongated as a result of a relative force between the syringe plunger 100 and the bung 102, as explained in greater detail below. Exemplary bungs 102 may comprise a resiliently deformable material, such as a rubberised material, permitting longitudinal deformation of the bung 102. The bung 102 may be configured such that longitudinal deformation thereof may alter the dimensions of the recess 110. In specific exemplary bungs 102, longitudinal elongation may increase a depth D of the recess 110, such that the engagement pin 112 may further enter the recess 110.

The barrel 104 of the syringe 106 comprises an aperture 124, a barrel sidewall 126 and a shoulder 128 between the aperture 124 and barrel sidewall 126 and defining an end of the barrel 104. The end of the barrel 104 may define a shape different to a base 130 of the bung 102. Exemplary barrels 104 may have an end defining a substantially conical shape or a substantially hemispherical shape.

FIG. 2b shows the syringe 106 after the syringe plunger 100 has travelled partly along its inward stroke. In FIG. 2b, the bung 102 has reached the end of the barrel 104. Due to the relative shapes of the end of the barrel 104 and the base 130 of the bung 102, a gap 132 exists between the base 130 of the bung 102 and the end of the barrel 104. The gap 132 may result in some of the contents of the barrel remaining therein after the inward stroke of the syringe plunger 100.

As the bung 102 has reached the end of the barrel 104, it cannot travel any further within the barrel 104. Therefore, continued force applied to the syringe plunger 100 produces a relative force between the end 108 of the syringe plunger 100 and the bung 102. The relative force urges the syringe plunger 100 further into the barrel 104. As the end 108 is slidably engaged within the recess 110 and the bung 102 is longitudinally deformable, the relative force pushes the deformation surface 116 of the engagement pin 112 against the base 120 of the recess 110. The recess sidewalls 118 are configured to stretch and that results in longitudinal deformation of the bung 102. That is, the relative force pushes the engagement pin 112 further into the recess 110, which results in the bung 102 being longitudinally deformed.

FIG. 2c shows the syringe 106 after the relative force has been applied and the bung 102 has been longitudinally deformed. The longitudinal deformation of the bung 102 has forced the base 130 of the bung into the gap 132, thereby ensuring that more (and possibly all) of the contents of the barrel 104 are expelled from the aperture 124. The depth D of the recess 110 has increased to accommodate more of the engagement pin 112. The base 130 of the bung 102 may be deformable to fit the shape defined by the end of the end of the barrel 104.

The skilled person may be able to envisage further exemplary embodiments without departing from the scope of the appended claims.

The invention claimed is:

1. A syringe plunger, comprising:
   an elongate shaft for insertion into a barrel of a syringe; and
   a bung having a recess formed therein,
      the recess comprising recess sidewalls,
   wherein an end of the elongate shaft comprises an engagement pin configured for slidable engagement within the recess in the bung such that a distal end of the engagement pin abuts a base of the recess,
      the engagement pin having a tapered shape that tapers down from a proximal end to the distal end, and
      the engagement pin configured to enter and exit the recess freely such that the engagement pin is not held within the recess, and
   wherein the engagement pin has a length greater than a depth of the recess in the bung such that, after engagement between the engagement pin and the recess, a relative force therebetween applied to the base of the recess of the bung causes further insertion of the engagement pin into the recess, longitudinally deforming the bung by stretching the recess sidewalls.

2. The syringe plunger according to claim 1, wherein the engagement pin comprises a substantially flat pin sidewall.

3. The syringe plunger according to claim 2, wherein the distal end of the engagement pin comprises a deformation surface configured to abut the base of the recess in the bung.

4. The syringe plunger according to claim 2, wherein the engagement pin has a conical or frusto-conical shape.

5. The syringe plunger according to claim 2, wherein the shaft further comprises a limiting shoulder configured to limit an insertion distance of the shaft within the recess of the bung.

6. The syringe plunger according to claim 1, wherein the distal end of the engagement pin comprises a deformation surface configured to abut the base of the recess in the bung.

7. The syringe plunger according to claim 6, wherein the engagement pin has a conical or frusto-conical shape.

8. The syringe plunger according to claim 1, wherein the engagement pin has a conical or frusto-conical shape.

9. The syringe plunger according to claim 1, wherein the shaft further comprises a limiting shoulder configured to limit an insertion distance of the shaft within the recess of the bung.

10. The syringe plunger according to claim 1, wherein the recess comprises substantially flat sidewalls.

11. The syringe plunger according to claim 10, wherein the recess has a conical or frusto-conical shape.

12. The syringe plunger according to claim 10, wherein the bung comprises a resiliently deformable material.

13. A syringe, comprising:
   a plunger; and a barrel configured to receive said plunger,
said plunger comprised of:
- an elongate shaft for insertion into the barrel of the syringe, and
- a bung having a recess formed therein,
  the recess comprising recess sidewalls, wherein an end of the elongate shaft comprises an engagement pin configured for slidable engagement within the recess in the bung such that a distal end of the engagement pin abuts a base of the recess,
- the engagement pin having a tapered shape that tapers down from a proximal end to the distal end, and
- the engagement pin configured to enter and exit the recess freely such that the engagement pin is not held within the recess, and wherein the engagement pin has a length greater than a depth of the recess in the bung such that, after engagement between the engagement pin and the recess, a relative force therebetween applied to the base of the recess of the bung causes further insertion of the engagement pin into the recess, longitudinally deforming the bung by stretching the recess sidewalls.

* * * * *